US007135583B2

(12) United States Patent
Han et al.

(10) Patent No.: US 7,135,583 B2
(45) Date of Patent: *Nov. 14, 2006

(54) PROCESS FOR PREPARATION OF ALKENYLPHOSPHINE OXIDES OR ALKENYLPHOSPHINIC ESTERS

(75) Inventors: Li-biao Han, Ibaraki (JP); Chang-qiu Zhao, Ibaraki (JP); Masato Tanaka, Ibaraki (JP)

(73) Assignees: Japan Science and Technology Corporation, Saitama (JP); National Institute of Advanced Industrial Science & Technology, Tokyo (JP)

( * ) Notice: Subject to any disclaimer, the term of this patent is extended or adjusted under 35 U.S.C. 154(b) by 315 days.

This patent is subject to a terminal disclaimer.

(21) Appl. No.: 10/467,411

(22) PCT Filed: Feb. 12, 2002

(86) PCT No.: PCT/JP02/01133

§ 371 (c)(1),
(2), (4) Date: Aug. 8, 2003

(87) PCT Pub. No.: WO02/064604

PCT Pub. Date: Aug. 22, 2002

(65) Prior Publication Data

US 2004/0059146 A1  Mar. 25, 2004

(30) Foreign Application Priority Data

Feb. 14, 2001 (JP) ............................. 2001-036365
Mar. 8, 2001 (JP) ............................. 2001-064707
Feb. 4, 2002 (JP) ............................. 2002-026495

(51) Int. Cl.
*C07F 9/40* (2006.01)
(52) U.S. Cl. ........................... 558/87; 558/73; 558/89; 558/117
(58) Field of Classification Search ................. 558/87, 558/70, 73, 89, 117
See application file for complete search history.

(56) References Cited

U.S. PATENT DOCUMENTS 5,693,826 A * 12/1997 Tanaka et al. ............... 549/6
6,111,127 A * 8/2000 Tanaka et al. ............. 558/137
6,949,667 B1 * 9/2005 Han et al. .................. 558/87

FOREIGN PATENT DOCUMENTS

| DE | 123 478 | 12/1976 |
| EP | 0 794 190 A1 | 9/1997 |
| JP | 2849712 B * | 11/1999 |
| JP | 2001-253888 A1 | 9/2001 |
| JP | 2001-316395 A1 | 11/2001 |

OTHER PUBLICATIONS

U.S. Appl. No. 10/471,093 by Applicant.*
International Preliminary Examination Report (English Translation).
International Search Report (English Translation).
Han, Li-Biao et al., "Oxadative Addition of HP(O)Ph2 to Platinum (0)and Palladium (0) Complexes and Palladium-Catalyzed Regio- and Stereoselective Hydrophosphinylation of Alkynes," Organometallics, The American Chemical Society, vol. 15, No. 15, pp. 3259-3261 (Jul. 23, 1996).
Supplementary Partial European Search Report (Dated Apr. 13, 2004).
Li-Biao Han et al., "Rhodium-catalyzed regi0- and Stereoselective Addition of Diphenylphoshine Oxide to Alkynes," Journal of Organic Chemistry, vol. 66, No. 17, pp. 5929-5932, American Chemical Society (Aug. 24, 2001).
Li-Biao Han et al., "Phosphinesaure-induzierte Umkehr der Regioslektivitat in dre Pd-katalysierten Hydrophosphinylierung von Alkinen mit Ph2P(OH)," Angewandte Chemie, vol. 110, No. 1/2, pp. 98-101, Wiley-VCH Verlag CmbH (1998).
Supplementary Partial European Search Report (Jul. 26, 2004).
Xu et al., "Palladium-Catalysed Synthesis of Alkyl Alkenylmethyl- and Alkenylphenylphosphinates," Synthesis, vol. 86, No. 3, pp. 240-242, Georg Thieme Verlag (Mar. 1986).
Molinari et al., "Synthesis of Optically Active β-Halogeno-Phosphinate Via Asymmetric Selection," Synthetic Communications, vol. 12, No. 10, pp. 749-753, Marcel Dekker Inc. (1982).
Database Crossfire Beilstein, 'Online!, Beilstein Institute zur Förderung der Chemischen Wissenschaften, Database Accession Nos. BRN 2733943 and BRN 2732850 (Jul. 1989) (Abstract Rasumow et al., J. Gen. Chem., USSR, vol. 35, p. 2038 (1965).
Database Crossfire Beilstein, 'Online!, Beilstein Institute zur Förderung der Chemischen Wissenschaften, Database Accession Nos. BRN 2734549, BRN 2733182, BRN 2727202 and BRN 2729139 (Jul. 1989) (Abstract of Anisimov et al, Bulletin Acad. Sci., USSR, Div. Chem. Sci., p. 410 (1962).

(Continued)

*Primary Examiner*—Kamal A. Saeed
*Assistant Examiner*—Susannah L. Chung
(74) *Attorney, Agent, or Firm*—Rader, Fishman & Grauer PLLC

(57) ABSTRACT

A novel process for preparation of alkenylphosphine oxides or alkenylphosphinic acid esters provided by which the objective compounds can be easily, safely and efficiently synthesized and easily separated and purified with little formation of by-products. Specifically, a process of conducting the addition reaction of an easily available secondary phosphine oxide or hydrogen phosphinic acid ester with an acetylene compound with a catalyst containing a Group 9 or 10 metal of the periodic table to thereby obtain the corresponding alkenylphosphine oxide or alkenylphosphinic acid ester.

18 Claims, No Drawings

OTHER PUBLICATIONS

Database Crossfire Beilstein, 'Online!, Beilstein Institute zur Förderung der Chemischen Wissenschaften, Database Accession Nos. BRN 2752587, BRN 2743436 and BRN 2729815 (Jul. 1989) (Abstract of Fedorova et al., Probl. Org. Sint, vol. 1965, pp. 258-263 (1965)).

Database Crossfire Beilstein, 'Online!, Beilstein Institute zur Förderung der Chemischen Wissenschaften, Database Accession No. BRN 2737163 (Jul. 1989) (Abstract of Timokhin et al., J. Gen. Chem., USSR, vol. 41, pp. 2658-2664 (1971)).

Database Crossfire Beilstein, 'Online!, Beilstein Institute zur Förderung der Chemischen Wissenschaften, Database Accession Nos. BRN 911971, BRN 909605, BRN 910614 and BRN 912456 (Jul. 1989) (Abstract of Gareev et al., J. Gen. Chem., USSR, vol. 47, pp. 2431-2440 (1977)).

Database Crossfire Beilstein, 'Online!, Beilstein Institute zur Förderung der Chemischen Wissenschaften, Database Accession No. BRN 2105316 (Jul. 1989) (Abstract of Gloyna et al., J. Prakt. Chem., vol. 319, p. 451-455 (1977)).

Database Crossfire Beilstein, 'Online!, Beilstein Institute zur Förderung der Chemischen Wissenschaften, Database Accession No. BRN 2717298 (Jul. 1989) (Abstract of Odinets et al., "Phosphorus, Sulfur, Silicon Relat. Elem.," vol. 51/52, p. 865 (1990)).

Database Crossfire Beilstein, 'Online!, Beilstein Institute zur Föederung der Chemischen Wissenschaften, Database Accession No. BRN 2722085 (Jul. 1989) (Abstract of Gefter et al., J. Gen. Chem., USSR, vol. 31, p. 883 (1961).

Database Crossfire Beilstein, 'Online!, Beilstein Institute zur Förderung der Chemischen Wissenschaften, Database Accession No. BRN 2722100 (Jul. 1989) (Abstract, Gefter et al., J. Gen. Chem., USSR, vol. 34, p. 88 (1964).

Database Crossfirre Beilstein, 'Online!, Beilstein Institute zur Förderung der Chemischen Wissenschaften, Database Accession No. BRN 2806352 (Jul. 1989) (Abstract of Kabachnik et al., J. Gen. Chem., USSR, vol. 32, pp. 3328-3296 (1962).

Database Crossfire Beilstein, 'Online!, Beilstein Institute zur Förderung der Chemischen Wissenschaften, Database Accession No. BRN 2936881 (Jul. 1989) (Abstract of Borisova et al., Dokl. Chem., vol. 226, pp. 142-145 (1976)).

Database Crossfire Beilstein, 'Online!, Beilstein Institute zur Förderung der Chemischen Wissenschaften, Database Accession No. BRN 2937634 (Jul. 1989) (Abstract of Gareev et al., J. Gen. Chem., USSR, vol. 47, p. 650 (1977)).

European Patent Office Examination Report for Application No. 02 711 453.7 dated Mar. 11, 2005.

Database Crossfire Beilstein, 'Online!, Beilstein Institute zur Förderung der Chemischen Wissenschaften, Database Accession No. BRN 2937635 (Jul. 1989) (Abstract of Gareev et al., J. Gen. Chem., USSR, vol. 47, p. 650 (1977)).

Database Crossfire Beilstein, 'Online!, Beilstein Institute zur Förderung der Chemischen Wissenschaften, Database Accession No. BRN 2937955 (Jul. 1989) (Abstract of King et al., J. Chem. Soc. Perkin Trans. 1, pp. 2226-2229 (1973)).

Database Crossfire Beilstein, 'Online!, Beilstein Institute zur Förderung der Chemischen Wissenschaften, Database Accession No. BRN 3007309 (Jul. 1989) (Abstract of Tschernyschew et al., Patent SU 415266 (1975).

Database Crossfire Beilstein, 'Online!, Beilstein Institute zur Förderung der Chemischen Wissenschaften, Database Accession No. BRN 3049251 (Jul. 1989) (Abstract of Gareev et al., J. Gen. Chem., USSR, vol. 49, pp. 442-444 (1979)).

Database Crossfire Beilstein, 'Online!, Beilstein Institute zur Förderung der Chemischen Wissenschaften, Database Accession No. BRN 3053273 (Jul. 1989) (Abstract of Rakov et al., J. Gen. Chem., USSR, vol. 45, pp. 1726-1728 (1975)).

Database Crossfire Beilstein, 'Online!, Beilstein Institute zur Förderung der Chemischen Wissenschaften, Database Accession No. BRN 3059725 (Jul. 1989) (Abstract of Rakov et al., J. Gen. Chem., USSR, vol. 45, pp. 1726-1728 (1975)).

Database Crossfire Beilstein, 'Online!, Beilstein Institute zur Föederung der Chemischen Wissenschaften, Database Accession No. BRN 3060381 (Jul. 1989) (Abstract of Gloyna et al., J. Prakt. Chem., vol. 319, pp. 451-453, 455-456 (1977)).

Database Crossfire Beilstein, 'Online!, Beilstein Institute zur Förderung der Chemischen Wissenachaften, Database Accession No. BRN 3061294 (Jul. 1989) (Abstract of Rakov et al., J. Gen. Chem., USSR, vol. 45, pp. 1726-1728 (1975)).

Database Crossfire Beilstein, 'Online!, Beilstein Institute zur Förderung der Chemischen Wissenschaften, Database Accession No. BRN 3061344 (Jul. 1989) (Abstract of Rakov et al., J. Gen. Chem., USSR, vol. 45, pp. 1726-1728 (1975)).

Database Crossfire Beilstein, 'Online!, Beilstein Institute zur Förderung der Chemischen Wissenschaften, Database Accession No. BRN 3062218 (Jul. 1989) (Abstract of Quast et al., J. Chem. Soc. Chem. Commun., pp. 390-391 (1979)).

Database Crossfire Beilstein, 'Online!, Beilstein Institute zur Förderung der Chemischen Wissenschaften, Database Accession No. BRN 3067220 (Jul. 1989) (Abstract of Quast et al., J. Chem. Soc. Chem Commun., pp. 390-391 (1979)).

Database Crossfirre Beilstein, 'Online!, Beilstein Institute zur Förderung der Chemischen Wissenschaften, Database Accession No. BRN 3070302 (Jul. 1989) (Abstract of Chemyshev et al., J. Gen. Chem., USSR, vol. 45, pp. 1733-1736 (1975)).

Database Crossfire Beilstein, 'Online!, Beilstein Institute zur Förderung der Chemischen Wissenschaften, Database Accession No. BRN 3075580 (Jul. 1989) (Abstract of Gloyna et al., J. Prakt. Chem., vol. 319, pp. 451-453, 455-456 (1977)).

Database Crossfire Beilstein, 'Online!, Beilstein Institute zur Förderung der Chemischen Wissenschaften, Database Accession No. BRN 3096083 (Jul. 1989) (Abstract of Moskva et al., J. Gen. Chem., USSR, vol. 39, pp. 2391-2393 (1969)).

Database Crossfire Beilstein, 'Online!, Beilstein Institute zur Förderung der Chemischen Wissenschaften, Database Accession No. BRN 3097523 (Jul. 1989) (Abstract of Moskva et al., J. Gen. Chem., USSR, vol. 39, pp. 2391-2393 (1969)).

Database Crossfire Beilstein, 'Online!, Beilstein Institute zur Förderung der Chemischen Wissenschaften, Database Accession No. BRN 4421272 (Dec. 1991) (Abstract of Xu et al., Synthesis, vol. 3, pp. 240-242 (1986)).

Database Crossfire Beilstein, 'Online!, Beilstein Institute zur Förderung der Chemischen Wissenschaften, Database Accession No. BRN 4452348 (Dec. 1991) (Abstract of Xu et al., Synthesis, vol. 3, pp. 240-242 (1986)).

Database Crossfire Beilstein, 'Online!, Beilstein Institute zur Förderung der Chemischen Wissenschaften, Database Accession No. BRN 5031021 (Aug. 1992) (Abstract of Russell et al., J. Amer. Chem. Soc., vol. 102, 25, pp. 7603-7604 (1980)).

Database Crossfire Beilstein, 'Online!, Beilstein Institute zur Förderung der Chemischen Wissenschaften, Database Accession No. BRN 5294169 (Aug. 1992) (Abstract of Lu et al., Synthesis, vol. 11, pp. 848-850 (1989)).

Database Crossfire Beilstein, 'Online!, Beilstein Institute zur Förderung der Chemischen Wissenschaften, Database Accession No. BRN 5294170 (Aug. 1992) (Abstract of Lu et al., Synthesis, vol. 11, pp. 848-850 (1989)).

Database Crossfire Beilstein, 'Online!, Beilstein Institute zur Förderung der Chemischen Wissenschaften, Database Accession No. BRN 5304203 (Aug. 1992) (Abstract of Lu et al., Synthesis, vol. 11, pp. 848-850 (1989)).

Database Crossfire Beilstein, 'Online!, Beilstein Institute zur Förderung der Chemischen Wissenschaften, Database Accession No. BRN 5304204 (Aug. 1992) (Abstract of Lu et al., Synthesis, vol. 11, pp. 848-850 (1989)).

Database Crossfire Beilstein, 'Online!, Beilstein Institute zur Förderung der Chemischen Wissenschaft, Database Accession No. BRN 5521636 (Feb. 1993) (Abstract of Grison et al., J. Organomet. Chem., vol. 662, 1-2, pp. 83-97 (2002)).

Database Crossfire Beilstein, 'Online!, Beilstein Institute zur Förderung der Chemischen Wissenschaften, Database Accession No. BRN 5545475 (Feb. 1993) (Abstract of Grison et al., J. Organomet. Chem., vol. 662, 1-2, pp. 83-97 (2002)).

Database Crossfire Beilstein, 'Online!, Beilstein Institute zur Förderung der Chemischen Wissenschaften, Database Accession No. BRN 5559299 (Feb. 1993) (Abstract of Kawashima et al., Chem. Lett., pp. 1883-1884 (1986)).

Database Crossfire Beilstein, 'Online!, Beilstein Institute zur Förderung der Chemischen Wissenschaften, Database Accession No. BRN 5870606 (Oct. 1993) (Abstract of Goebel et al., Phosphorus, Sulfur Silicon Relat. Elem., vol. 73, 1-4, pp. 67-80 (1992).

Database Crossfire Beilstein, 'Online!, Beilstein Institute zur Förderung der Chemischen Wissenschaften, Database Accession No. BRN 5946434 (Jul. 1993) (Abstract of Lapin et al., J. Gen. Chem., USSR, vol. 51, 4, pp. 659-665 (1981)).

Database Crossfire Beilstein, 'Online!, Beilstein Institute zur Förderung der Chemischen Wissenschaften, Database Accession No. BRN 6175165 (Oct. 1993) (Abstract of Carey et al., J. Chem. Soc. Perkin Trans. 1, vol. 7, pp. 831-840 (1993)).

Database Crossfire Beilstein, 'Online!, Beilstein Institute zur Förderung der Chemischen Wissenschaften, Database Accession No. BRN 6175166 (Oct. 1993) (Abstract of Carey et al., J. Chem. Soc. Perkin Trans. 1, vol. 7, pp. 831-840 (1993)).

Database Crossfire Beilstein, 'Online!, Beilstein Institute zur Förderung der Chemischen Wissenschaften, Database Accession No. BRN 6176268 (Oct. 1993) (Abstract of Carey et al., J. Chem. Soc. Perkin Trans. 1, vol. 7, pp. 831-840 (1993)).

Database Crossfire Beilstein, 'Online!, Beilstein Institute zur Förderung der Chemischen Wissenschaften, Database Accession No. BRN 6176269 (Oct. 1993) (Abstract of Carey et al., J. Chem. Soc. Perkin Trans. 1, vol. 7, pp. 831-840 (1993)).

Database Crossfire Beilstein, 'Online!, Beilstein Institute zur Föederung der Chemischen Wissenschaften, Database Accession No. BRN 6214037 (Oct. 1993) (Abstract of Inokawa et al., Phosphorus Sulfur, vol. 16, pp. 79-82 (1983)).

Database Crossfire Beilstein, 'Online!, Beilstein Institute zur Förderung der Chemischen Wissenschaften, Database Accession No. BRN 6875729 (Oct. 1994) (Abstract of Abdulganeeva et al., J. Gen. Chem., USSR, vol. 56, pp. 1100-1104 (1986)).

Database Crossfire Beilstein, 'Online!, Beilstein Institute zur Förderung der Chemischen Wissenschaften, Database Accession No. BRN 6877850 (Oct. 1994) (Abstract of Abdulganeeva et al., J. Gen. Chem., USSR, vol. 56, pp. 1100-1104 (1986)).

Database Crossfire Beilstein, 'Online!, Beilstein Institute zur Förderung der Chemischen Wissenschaften, Database Accession No. BRN 6878820 (Oct. 1994) (Abstract of Abdulganeeva et al., J. Gen. Chem., USSR, vol. 56, pp. 1100-1104 (1986)).

Database Crossfire Beilstein, 'Online!, Beilstein Institute zur Förderung der Chemischen Wissenschaften, Database Accession No. BRN 7530787 (Feb. 1997) (Abstract of Morise et al., J. Chem. Soc. Perkin Trans. 1, vol. 17, pp. 2179-2186 (1996)).

Database Crossfire Beilstein, 'Online!, Beilstein Institute zur Förderung der Chemischen Wissenschaften, Database Accession No. BRN 7531418 (Feb. 1997) (Abstract of Morise et al., J. Chem. Soc. Perkin Trans. 1, vol. 17, pp. 2179-2186 (1996)).

Database Crossfire Beilstein, 'Online!, Beilstein Institute zur Förderung der Chemischen Wissenschaften, Database Accession No. BRN 7767278 (Mar. 1998) (Abstract of Zymanczyk-Duda et al., Phosphorus, Sulfur Silicon Relat. Elem., vol. 112, pp. 47-56 (1996)).

Database Crossfire Beilstein, 'Online!, Beilstein Institute zur Förderung der Chemischen Wissenschaften, Database Accession No. BRN 8202311 (Feb. 2000) (Abstract of Krawczyk et al., Phosphorus, Sulfur Silicon Relat. Elem., vol. 132, pp. 135-146 (1998)).

Database Crossfire Beilstein, 'Online!, Beilstein Institute zur Förderung der Chemischen Wissenschaften, Database Accession No. BRN 8204275 (Feb. 2000) (Abstract of Krawczyk et al., Phosphorus, Sulfur Silicon Relat. Elem., vol. 132, pp. 135-146 (1998).

Database Crossfire Beilstein, 'Online!, Beilstein Institute zur Förderung der Chemischen Wissenschaften, Database Accession No. BRN 8206402 (Feb. 2000) (Abstract of Krawczyk et al., Phosphorus, Sulfur Silicon Relat. Elem., vol. 132, pp. 135-146 (1998)).

Database Crossfire Beilstein, 'Online!, Beilstein Institute zur Förderung der Chemischen Wissenschaften, Database Accession No. BRN 8206689 (Feb. 2000) (Abstract of Krawczyk et al., Phosphorus, Sulfur Silicon Relat. Elem., vol. 132, pp. 135-146 (1998)).

Database Crossfire Beilstein, 'Online!, Beilstein Institute zur Förderung der Chemischen Wissenschaften, Database Accession No. BRN 8206691 (Feb. 2000) (Abstract of Krawczyk et al., Phosphorus, Sulfur Silicon Relat. Elem., vol. 132, pp. 135-146 (1998)).

Database Crossfire Beilstein, 'Online!, Beilstein Institute zur Förderung der Chemischen Wissenschaften, Database Accession NO. BRN 8212205 (Feb. 2000) (Abstract of Krawczyk et al., Phosphorus, Sulfur Silicon Relat. Elem., vol. 132, pp. 135-146 (1998)).

* cited by examiner

PROCESS FOR PREPARATION OF ALKENYLPHOSPHINE OXIDES OR ALKENYLPHOSPHINIC ESTERS

TECHNICAL FIELD

The present invention relates to a process for the preparation of alkenylphosphine oxides or alkenylphosphinic acid esters.

These compounds are a group of compounds which are highly useful in view of synthesis of fine chemicals in such a manner, for instance, they are able to be easily converted to tertiary phosphines and they themselves easily react with nucleophilic agents and radical species. In addition, they are able to be used for Horner-Witting reaction.

Furthermore, it is known that Alkenylphosphinic acid skeletons are found in nature and that they themselves exhibit a physiological action through interaction with enzymes, etc.

BACKGROUND OF THE INVENTION

With regard to a method for the synthesis of alkenylphosphine oxides, there have been known a method where an organic metal reagent such as an alkenyl Grignard reagent is made to react with a phosphorus halide compound, a method where secondary phosphine oxide is made to react with an alkenyl halogen compound, etc. However, in the former method, there is a disadvantage that it is accompanied with production of salt of magnesium, etc. while, in the latter method, it is necessary that a base is added so as to trap the generated hydrogen halide as a salt. In addition, both of those methods are not preferred from an industrial view in such a respect that other compounds besides the desired compound are also formed as by-product.

In the meanwhile, it has been recently found a method where a secondary phosphine oxide added to an acetylene compound in the presence of a palladium catalyst (*Orgnometallics*, volume 15, page 3259, 1996; Japanese Patent No. 2,849,712) but selectively of the product is not high in this method.

With regard to a method for the synthesis of alkenylphosphinic acid esters through carbon-phosphorus bond forming reaction, the most general method is a substitution reaction of the corresponding alkenyl halide compound with a hydrogen phosphinic acid ester. However, in this method, it is necessary to add a base for trapping of hydrogen halide which is produced simultaneously as a result of the reaction whereby large quantities of hydrogen halide salt are produced at the same time. In addition, the alkenyl halide compound which is a starting material therefor is not always easily available industrially and, further, it usually has toxicity. Therefore, the method is never a method which is industrially advantageous.

DISCLOSURE OF THE INVENTION

The present invention has been achieved in view of the above-mentioned current status and its object is to provide a novel production process for alkenylphosphine oxides or alkenylphosphinic acid esters where the products can be easily, safely and efficiently synthesized, by-products are little and separation and purification are easy.

The present inventors have carried out an intensive study for the reaction of an easily-available secondary phosphine oxide or hydrogen phosphinic acid ester with an acetylene compound and, as a result, they have found that the addition reaction proceeds in the presence of a specific catalyst giving the corresponding alkenylphosphine oxide or alkenylphosphinic acid ester easily. On the basis of such a fact, the present invention has been accomplished.

Thus, in accordance with the present invention, there is provided a process for the production of an alkenylphosphine oxide compound (when $R_0^4$ is $R^4$) and alkenylphosphinic acid ester compound (when $R_0^4$ is $OR^4$) represented by the formula [III]

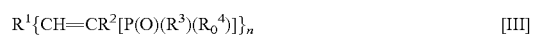

$$R^1\{CH{=}CR^2[P(O)(R^3)(R_0^4)]\}_n \qquad [III]$$

and/or the formula [IV]

$$R^1\{C[P(O)(R^3)(R_0^4)]{=}CHR^2\}_n \qquad [IV]$$

($R^1$, $R^2$, $R^3$ and $R_0^4$ are the same as those defined below), characterized in that, a catalyst containing a metal of group 9 or group 10 of the periodic table is used and an acetylene compound represented by the formula [I]

$$R^1(C{\equiv}CR^2)_n \qquad [I]$$

(in the formula, n is 1 or 2; $R^1$ and $R^2$ each when n is 1 and $R^2$ when n is 2 is hydrogen atom, an optionally substituted alkyl group, an optionally substituted cycloalkyl group, an optionally substituted alkenyl group, an optionally substituted cycloalkenyl group, an optionally substituted aryl group, an optionally substituted aralkyl group, an optionally substituted aryloxy group, an optionally substituted heteroaryl group, a ferrocenyl group, an optionally substituted alkoxy group or an optionally substituted silyl group; and $R^1$ when n is 2 is an optionally substituted alkylene group, an optionally substituted cycloalkylene group, an optionally substituted alkenylene group, an optionally substituted cycloalkenylene group, an optionally substituted arylene group, an optionally substituted aralkylene group, an optionally substituted arylenedioxy group, an optionally substituted heteroarylene group, a ferrocenylene group, an optionally substituted alkylenedioxy group or an optionally substituted silylenedioxy group) is made to react with a compound represented by the formula [II]

$$HP(O)(R^3)(R_0^4) \qquad [II]$$

[in the formula, $R^3$ is an alkyl group, a cycloalkyl group, an aralkyl group or an aryl group; and $R_0^4$ is $R^4$ or $OR^4$ (where $R^4$ is an alkyl group, a cycloalkyl group, an aralkyl group or an aryl group)].

BEST MODE FOR CARRYING OUT THE INVENTION

In the production process according to the present invention, the acetylene compound used as a starting material is represented by the above-mentioned [I] where $R^1$ and $R^2$ each when n is 1 and $R^2$ when n is 2 is hydrogen atom, an optionally substituted alkyl group, an optionally substituted cycloalkyl group, an optionally substituted alkenyl group, an optionally substituted cycloalkenyl group, an optionally substituted aryl group, an optionally substituted aralkyl group, an optionally substituted aryloxy group, an optionally substituted heteroaryl group, a ferrocenyl group, an optionally substituted alkoxy group or an optionally substituted silyl group.

With regard to the alkyl group when $R^1$ and/or $R^2$ in the formula [I], the formula [III] and the formula [IV] are/is optionally substituted alkyl(s), there may be exemplified a straight-chain or branched alkyl group having 1~20, preferably 1~10 or, more preferably, 1~6 carbon(s). To be more specific, methyl group, ethyl group, propyl group, isopropyl group, butyl group, isobutyl group, sec-butyl group, tert-butyl group, pentyl group, hexyl group, etc. may be exemplified.

With regard to a cycloalkyl group of the optionally substituted cycloalkyl group, there may be exemplified a monocyclic, polycyclic or fused-ring cycloalkyl group having 3~30, preferably 3~20 or, more preferably, 3~10 carbons. To be more specific, cyclopropyl group, cyclopentyl group, cyclohexyl group, cyclooctyl group, etc. may be exemplified.

With regard to an alkenyl group of the optionally substituted alkenyl group, there may be exemplified a group where the above-mentioned alkyl group having 2 or more carbons has one or more unsaturated groups such as a double bond. To be more specific, vinyl group, allyl group, 1-propenyl group, isopropenyl group, 2-butenyl group, 1,3-butadienyl group, 2-pentenyl group, 2-hexenyl group, etc. may be exemplified.

With regard to a cycloalkenyl group of the optionally substituted cycloalkenyl group, there may be exemplified a group where the above-mentioned cycloalkyl group has one or more unsaturated group(s) such as double bond. To be more specific, cyclopropenyl group, cyclopentenyl group, cyclohexenyl group, etc. may be exemplified.

With regard to an aryl group of the optionally substituted aryl group, there may be exemplified a monocyclic, polycyclic or fused-ring aromatic hydrocarbon group having 6~30, preferably 6~20 or, more preferably, 6~14 carbons. To be more specific, phenyl group, tolyl group, xylyl group, naphthyl group, methylnaphthyl group, anthryl group, phenanthryl group, biphenyl group, etc. may be exemplified.

With regard to an aralkyl group of the optionally substituted aralkyl group, there maybe exemplified a monocyclic, polycyclic or fused-ring aralkyl group having 7~30, preferably 7~20 or, more preferably, 7~15 carbons. To be more specific, benzyl group, phenethyl group, naphthylmethyl group, naphthylethyl group, etc. may be exemplified.

With regard to an aryloxy group of the optionally substituted aryloxy group, there may be exemplified an aryloxy group having a monocyclic, polycyclic or fused-ring aromatic hydrocarbon group having 6~30, preferably 6~20 or, more preferably, 6~14 carbons. To be more specific, phenoxy group, tolyloxy group, xylyloxy group, naphthoxy group, methylnaphthyloxy group, anthryloxy group, phenanthryloxy group, biphenyloxy group, etc. may be exemplified.

With regard to a heteroaryl group of the optionally substituted heteroaryl group, there maybe exemplified various kinds of heteroaromatic ring groups containing hetero atoms such as oxygen, nitrogen and sulfur and numbers of carbons contained therein are usually 4~12 and, preferably, 4~8. Specific examples thereof are thienyl group, furyl group, pyridyl group and pyrrolyl group.

With regard to an alkoxy group of the optionally substituted alkoxy group, there may be exemplified an alkoxy group having 1~8 or, preferably, 1~4 carbon(s) and specific examples thereof are methoxy group, ethoxy group and butoxy group.

With regard to a substituent for those alkyl group, cycloalkyl group, alkenyl group, cycloalkenyl group, aryl group, aralkyl group, aryloxy group, heteroaryl group and alkoxy group, there may be exemplified an alkyl group; hydroxyl group; an alkoxy group such as methoxy group, ethoxy group, propoxy group and butoxy group; a halogen atom such as chlorine, bromine and fluorine; cyano group; a dialkylamino group such as dimethylamino group and diethylamino group; an alkoxycarbonyl group such as methoxycarbonyl group and ethoxycarbonyl group; silyl group; a substituted silyl group such as trimethylsilyl group, triethylsilyl group, tert-butyldimethylsilyl group and triphenylsilyl group; and a siloxy group such as tert-butyldimethylsiloxy group.

With regard to a silyl group of the optionally substituted silyl group, that which is substituted, for example, with alkyl, aryl, aralkyl and alkoxy groups may be covered as well. Specific examples thereof are trimethylsilyl group, triethylsilyl group, triphenylsilyl group, phenyldimethylsilyl group, trimethoxysilyl group and tert-butyldimethylsilyl group.

The optionally substituted alkylene group, the optionally substituted cycloalkylene group, the optionally substituted alkenylene group, the optionally substituted cycloalkenylene group, the optionally substituted arylene group, the optionally substituted aralkylene group, the optionally substituted arylenedioxy group, the optionally substituted heteroarylene group, the ferrocenylene group, the optionally substituted alkylenedioxy group or the optionally substituted silylenedioxy group represented by $R^1$ in case n is 2 is selected from a divalent residue where one hydrogen atom is removed from the already-mentioned $R^1$ when n is 1 or a divalent residue where one hydrogen atom is substituted with one oxygen atom in the $R^1$ and specific examples thereof are methylene group, ethylene group, trimethylene group, methylethylene group, propylene group, tetramethylene group, 1,2-dimethylethylene group, pentamethylene group, hexamethylene group, cyclohexylene group, phenylene group, naphthylene group, furandiyl group, ferrocenylene group, 2-butenediyl group, tetramethylenedioxy group, phenylenedioxy group and dimethylsilylene group.

Examples of the acetylene compound which is preferably used in the production process of the present invention are unsubstituted acetylene, methylacetylene, butyne, 1-hexyne, 2-hexyne, 1-octyne, 4-octyne, 1-butyn-4-ol, 2-butyn-1-ol, 3-butyn-1-ol, 5-hexyn-1-ol, 1-octyn-3-ol, 5-chloro-1-pentyne, phenylacetylene, trimethylsilylacetylene, ethynylthiophene, hexynonitrile, cyclohexenylacetylene, ethynylferrocene, 1,4-pentadiyne, 1,8-nonadiyne and diethynylbenzene although they are non-limitative.

The secondary phosphine oxide or hydrogen phosphinic acid ester used as a starting material in the production process of the present invention is represented by the already-mentioned formula [II]. In the formula, $R^3$ and $R^4$ each independently is an alkyl group, a cycloalkyl group, an aralkyl group or an aryl group.

With regard to the alkyl group, the cycloalkyl group, the aralkyl group or the aryl group represented by $R^3$ and $R^4$ in the formulae [II], [III] and [IV], the same ones as those listed in the above passage for $R^1$ and $R^2$ may be exemplified.

Specific examples of the preferred secondary phosphine oxide are diphenylphosphine oxide, etc. Specific examples of the preferred hydrogen phosphinic acid ester are ethyl phenylphosphinate and cyclohexyl phenylphosphinate although they are non-limitative.

Ratio of the acetylene compound to the secondary phosphine oxide compound or the hydrogen phosphinic acid ester compound used is usually preferred to be 1:1 in terms of their molar ratio although occurrence of the reaction is not inhibited even when the ratio is smaller or larger than that.

In order to carry out the reaction of the present invention, it is preferred to use a catalyst containing metal of group 9 or group 10 of the periodic table and it is possible to use a single substance containing palladium or rhodium or a catalyst where such a metal is carried on activated charcoal, silica or the like. It is also possible to use a complex catalyst containing rhodium or palladium. With regard to such a complex catalyst, although that of various structures may be used, preferred ones are those having the so-called low valence and those which have tertiary phosphine or tertiary phosphite as a ligand are preferred embodiments as well. It is also a preferred embodiment to use a precursor which is easily converted to a low valence in the reaction system. Further, a process where a complex containing neither tertiary phosphine nor tertiary phosphite as a ligand is mixed with tertiary phosphine or phosphite in the reaction system to form a low valence complex having tertiary phosphine or phosphite as a ligand in the reaction system is a preferred embodiment as well. With regard to a ligand which achieves an advantageous efficiency in any of those methods, there may be exemplified various tertiary phosphines and tertiary phosphites.

Examples of the ligand which can be preferably used in the present invention are triphenylphosphine, diphenylmethylphosphine, phenyldimethylphosphine, 1,4-bis(diphenylphosphino)butane, 1,3-bis(diphenylphosphino)propane, 1,2-bis(diphenylphosphino)ethane, 1,1'-bis(diphenylphosphino)ferrocene, trimethyl phosphite and triphenyl phosphite.

With regard to the complex containing neither tertiary phosphine nor tertiary phosphite which is used together therewith, there may be exemplified acetylacetonatobis(ethylene)rhodium, a chlorobis(ethylene)rhodium dimer, dicarbonyl(acetylacetonato)rhodium, hexarhodiumhexadecacarbonyl, chloro(1,5-cyclooctadiene)rhodium dimer, a chloro (norbornadiene)rhodium dimer, bis(dibenzylideneacetone) palladium and palladium acetate although they are non-limitative.

With regard to the preferably used phosphine or phosphite complex, there may be exemplified chlorocarbonylbis(triphenylphosphine)rhodium, hydridecarbonyltris(triphenylphosphine)rhodium, chlorotris(triphenylphosphine)rhodium, bromotris(triphenylphosphine)rhodium, chlorocarbonylbis(triphenylphosphite)rhodium, dimethylbis(triphenylphosphine)palladium, dimethylbis(diphenylmethylphosphine) palladium, dimethylbis(dimethylphenylphosphine) palladium, dimethylbis(triethylphosphine)palladium, (ethylene)bis(triphenylphosphine)palladium, tetrakis(triphenylphosphine)palladium and dichlorobis(triphenylphosphine)palladium.

In order to carry out the reaction of the present invention for the production of alkenylphosphine oxide, it is particularly preferred to use a rhodium catalyst.

With regard to the rhodium catalyst, it is possible to use that of various structures such as metallic rhodium species and rhodium compound.

With regard to the metallic rhodium species, there may be exemplified rhodium black, rhodium powder and rhodium which is carried on a carrier such as rhodium carried on alumina, rhodium carried on silica and rhodium carried on activated carbon.

With regard to the rhodium compound, there may be used any of compounds of mono- to trivalent rhodium and any of complex containing no ligand and complex where ligand such as tertiary phosphine and tertiary phosphite is coordinated thereto. Examples thereof are rhodium salts such as a rhodium acetate dimer, rhodiumhalide (such as rhodium chloride, rhodium bromide and rhodium iodide) and rhodium acetylacetonate, organorhodium compounds such as acetylacetonatobis(ethylene)rhodium, a chlorobis(ethylene)rhodium dimer, dicarbonyl(acetylacetonato)rhodium, hexarhodiumhexadecacarbonyl, chloro(1,5-cyclooctadiene) rhodium dimer, chloro(norbornadiene)rhodium dimer and chloro(1,5-hexadiene)rhodium dimmer, and rhodium complexes such as chlorocarbonylbis(triphenylphosphine) rhodium, hydridocarbonyltris(triphenylphosphine)rhodium, chlorotris(triphenylphosphine)rhodium, bromotris(triphenylphosphine)rhodium, iodotris(triphenylphosphine) rhodium, chlorocarbonylbis(trimethyl phosphite)rhodium, bromotris(triphenylphosphine)rhodium, chloro(1,5-cyclooctadienyl)(triphenylphosphine)rhodium and trichlorotris(pyridine)rhodium although they are non-limitative.

A method where a rhodium complex containing neither tertiary phosphine nor tertiary phosphite is used together with tertiary phosphine or tertiary phosphite to generate a rhodium complex having tertiary phosphine or tertiary phosphite in the reaction system, and to use the resulting rhodium species as a catalyst is a preferred embodiment as well.

Further, a method where a rhodium complex which is formed in a reaction system wherein a base such as amine is added to a rhodium complex containing no ligand is used as a catalyst is a preferred embodiment as well.

In order to efficiently carry out the reaction of the present invention for the production of the alkenylphosphinic acid ester compound, a complex catalyst of low valence is preferred and a complex catalyst of low valence containing rhodium or palladium where tertiary phosphine or tertiary phosphite is a ligand is particularly preferred. It is also a preferred embodiment to use a precursor which is easily converted to low valence in the reaction system. Further, it is also a preferred embodiment that, in the reaction system, a complex containing neither tertiary phosphine nor tertiary phosphite is mixed with a tertiary phosphine or phosphite and a low valence complex where tertiary phosphine or phosphite is a ligand is formed in the reaction system.

In the reaction of the present invention where alkenylphosphinic acid ester compounds are produced, palladium catalyst, rhodium catalyst, etc. show the activity even when used alone although it is also possible to use together with a phosphinic acid additive. In particular, in the reaction where regioisomers are produced, regioselectivity becomes high by the joint use with a phosphinic acid additive and, therefore, it is preferred to use jointly in such a case. Such a phosphinic acid is represented, for example, by the formula [V].

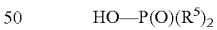　　　[V]

(In the formula, $R^5$ is an alkyl group, a cycloalkyl group or an aryl group.)

In the formula [V] where $R^5$ is an alkyl group, examples of the alkyl group are alkyl groups having 1~6 or, preferably, 1~4 carbon(s). Specific examples thereof are methyl, ethyl, n- or isopropyl group, n-, iso-, sec- or tert-butyl group, n-pentyl group and n-hexyl group.

When it is a cycloalkyl group, examples of the cycloalkyl group are cycloalkyl groups having 3~12 or, preferably, 5~6 carbons and specific examples thereof are cyclopentyl group and cyclohexyl group.

When it is an aryl group, examples of the aryl group are aryl groups having 6~14 or, preferably, 6~10 carbons. Specific examples thereof are phenyl group and naphthyl group and there are also included substituted groups thereof (such as tolyl group, xylyl group and benzylphenyl group).

The alkyl, cycloalkyl or aryl group represented by $R^5$ may be substituted with a functional group which is inert to the reaction, such as methoxy group, methoxycarbonyl group, cyano group, dimethylamino group, fluoro group, chloro group and hydroxyl group.

Specific examples of the phosphinic acid used in the present invention are diphenylphosphinic acid and dimethylphosphinic acid. The amount of phosphinic acid relative to the hydrogen phosphinic acid ester used is equimolar or less or, preferably, 0.1~10 molar %.

With regard to the above-mentioned catalysts used in the reaction of the present invention, one or more thereof is/are appropriately selected and used depending upon the reaction.

The amount of such a catalyst used may be a so-called catalytic amount. Generally, the amount relative to the acetylene compound is 20 molar % or less and, usually, 5 molar % or less is sufficient.

Molar ratio of the acetylene compound or the diacetylene compound to the secondary phosphine oxide or the hydrogen phosphinic acidester in the reaction is not particularly limited but is usually 1:1 although the occurrence of the reaction is not disturbed even when the ratio is more or is less than that.

Although there is no particular need of using a solvent in the reaction of the present invention, it is also possible to carry out the reaction in a solvent if necessary. With regard to the solvent, there may be used various ones such as hydrocarbons, halogenated hydrocarbons, ethers, ketones, nitrites and esters. Each of them may be used solely or two or more thereof may be used as a mixture thereof.

With regard to the reaction temperature, the reaction does not proceed at an advantageous rate when it is too low while, when it is too high, the catalyst decomposes. Therefore, it is generally selected from the range of –20° C.~300° C. and, preferably, it is carried out within a range of from room temperature to 150° C.

The catalyst used in the present invention is sensitive to oxygen and it is preferred to carry out the reaction in an atmosphere of inert gas such as nitrogen, argon or methane. Separation of the product from the reaction mixture can be easily achieved by means of chromatography, distillation, recrystallization, etc.

The present invention will now be more specifically illustrated by way of the following Examples although the present invention is not limited by those Examples at all.

EXAMPLES

Example 1

To 1 ml of toluene were added 1 mmol of diphenylphosphine oxide, 1 mmol of 1-octyne and 3 molar % of RhCl(PPh$_3$)$_3$ as a catalyst followed by subjecting to a reaction in a nitrogen atmosphere at room temperature for 1 hour. The reaction solution is concentrated and then isolated and purified by means of liquid chromatography to give [(E)-1-octen-1-yl]diphenylphosphine oxide in a yield of 70%.

This compound is a known compound and its structure was determined by means of comparison with an authentic sample which was separately synthesized.

Example 2

The reaction was carried out under the same conditions as in Example 1 using an RhBr(PPh$_3$)$_3$ catalyst whereupon, after 1 hour, the product [(E)-1-octen-1-yl]diphenylphosphine oxide was obtained in a yield of 95%.

Example 3

The reaction was carried out under the same conditions as in Example 1 using an RhI(PPh$_3$)$_3$ catalyst whereupon, after 1 hour, the product [(E)-1-octen-1-yl]diphenylphosphine oxide was obtained in a yield of 100%.

Example 4

The reaction was carried out under the same conditions as in Example 1 using an RhCl(CO)(PPh$_3$)$_2$ catalyst at 80° C. whereupon, after 0.5 hour, the product [(E)-1-octen-1-yl]diphenylphosphine oxide was obtained in a yield of 89%.

Example 5

The reaction was carried out under the same conditions as in Example 1 using an RhH(CO)(PPh$_3$)$_3$ catalyst at 80° C. whereupon, after 0.5 hour, the product [(E)-1-octen-1-yl]diphenylphosphine oxide was obtained in a yield of 87%.

Example 6

The reaction was carried out under the same conditions as in Example 1 using an RhCl(cod)$_2$ catalyst at room temperature whereupon, after 1 hour, the product [(E)-1-octen-1-yl]diphenylphosphine oxide was obtained in a yield of 65%.

Example 7

The reaction was carried out under the same conditions as in Example 1 using a dicarbonyl(acetylacetonato)rhodium (I) catalyst at 80° C. whereupon, after 1.5 hours, the product [(E)-1-octen-1-yl]diphenylphosphine oxide was obtained in a yield of 32%.

Example 8

The reaction was carried out under the same conditions as in Example 1 using an ethylene(acetylacetonato)rhodium (I) catalyst at 80° C. whereupon, after 1.5 hours, the product [(E)-1-octen-1-yl]diphenylphosphine oxide was obtained in a yield of 67%.

Example 9

The reaction was carried out under the same conditions as in Example 1 using an [Rh(OAc)$_2$]$_2$ catalyst at 80° C. whereupon, after 1.5 hours, the product [(E)-1-octen-1-yl]diphenylphosphine oxide was obtained in a yield of 12%.

Example 10

The reaction was carried out under the same conditions as in Example 1 using a rhodium chloride catalyst by addition of 2 ml of ethanol and 4 mmol of triethylamine at 80° C.

whereupon, after 3 hours, the product [(E)-1-octen-1-yl]diphenylphosphine oxide was obtained in a yield of 97%.

Example 11

The reaction was carried out under the same conditions as in Example 1 using rhodium carried on activated carbon (5% rhodium being carried) at 110° C. whereupon, after 7 hours, the product [(E)-1-octen-1-yl]diphenylphosphine oxide was obtained in a yield of 91%.

Examples 12~25

Various kinds of alkenylphosphine oxides were synthesized using various acetylene compounds by the same means as in Example 1. The result is summarized in Table 1.

TABLE 1

| Examples | Acetylene | Products | Yields (%) |
|---|---|---|---|
| 12 |  | 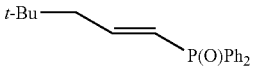 | 93 |
| 13 | 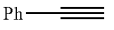 | 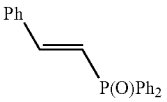 | 89 |
| 14 | 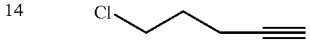 | 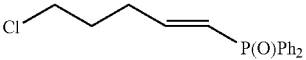 | 88 |
| 15 | 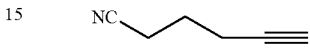 | 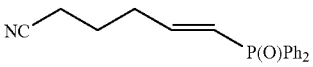 | 92 |
| 16 | 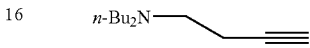 | 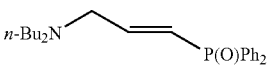 | 86 |
| 17 | 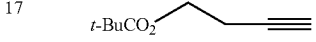 | 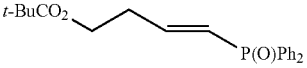 | 87 |
| 18 | 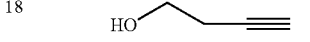 | 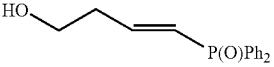 | 94 |
| 19 |  | 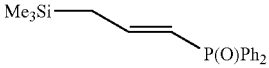 | 85 |
| 20 | 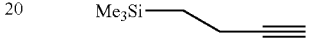 | 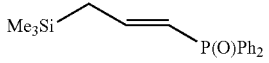 | 81 |
| 21 | 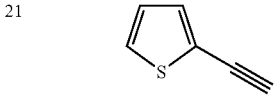 | 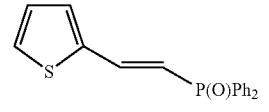 | 92 |
| 22 | 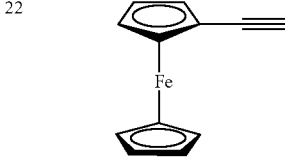 | 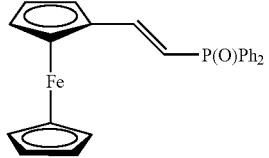 | 93 |
| 23 | 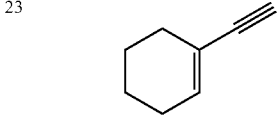 | 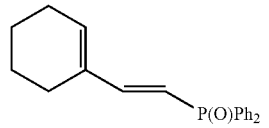 | 94 |
| 24 | 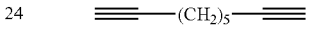 | 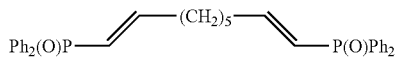 | 76 |

TABLE 1-continued

| Examples | Acetylene | Products | Yields (%) |
|---|---|---|---|
| 25 | CH₃CH₂CH₂-C≡C-CH₂CH₂CH₃ | CH₃CH₂CH₂CH=C(P(O)Ph₂)CH₂CH₂CH₃ | 91 |

Example 26

To 2 ml of toluene under a nitrogen atmosphere were added 10 molar % of diphenylphosphinic acid, 1 mmol of ethyl phenylphosphinate, 1 mmol of 1-octyne and 5 molar % of Me₂Pd(PPhMe₂)₂ as a catalyst and the mixture was subjected to a reaction at 80° C. for 5 hours to give a mixture of ethyl phenyl[(E)-1-octen-1-yl]phosphinate and ethyl phenyl(1-octen-2-yl)phosphinate (ratio=4:96) in a yield of 96%.

The latter compound is a novel compound which has not been mentioned in literatures. The spectral data of ethyl phenyl(1-octen-2-yl)phosphinate are as follows.

$^1$H NMR (500 MHz, CDCl$_3$) δ 7.69~7.73 (m, 2H), 7.45~7.46 (m, 1H), 7.39~7.41 (m, 2H), 5.91 (dd, 1H, $J_{HP}$=21.4 Hz, J=1.2 Hz), 5.71 (dd, 1H, $J_{HP}$=44.0 Hz, J=1.2 Hz), 3.93~4.04 (m, 2H), 2.10~2.13 (m, 2H), 1.34~1.36 (m, 2H), 1.28 (t, 3H, J=7.0 Hz), 1.13~1.19 (m, 4H), 0.77 (t, 3H, J=7.0 Hz).

$^{13}$C NMR (125.4 MHz, CDCl$_3$) δ 142.78($J_{CP}$=121.9 Hz), 132.12, 131.83, 130.73 ($J_{CP}$=131.2 Hz), 128.47, 128.08, 60.80, 31.56, 31.43, 28.80, 27.91, 22.54, 16.51, 14.04.

$^{31}$P NMR (201.9 MHz), CDCl$_3$) δ 33.26.

HRMS as C$_{16}$H$_{25}$O$_2$P, calculated: 280.1592, found: 280.1581.

Example 27

In toluene (2 ml)under a nitrogen atmosphere at 100° C. for 20 hours, 1 mmol of cyclohexyl phenylphosphinate and 1 mmol of 1-octene were allowed to react using 3 molar % of Rh(PPh$_3$)$_3$Br as a catalyst to give cyclohexyl phenyl[(E)-1-octen-1-yl]phosphinate in a yield of 98%.

Example 28

The reaction of Example 26 was carried out without addition of diphenylphosphinic acid and, as a result, a mixture (ratio=44:56) of ethyl phenyl[(E)-1-octen-1-yl]phosphinate and ethyl phenyl(1-octen-2-yl)phosphinate was obtained in a yield of 71%.

Examples 29~38

Various kinds of alkenylphosphinic acid esters were synthesized by the same means as in Example 26 using various acetylene compounds. The result is summarized in Table 2.

TABLE 2

| Examples | Alkynes | Adducts | Yields (%) |
|---|---|---|---|
| 29 | HC≡CH | CH₂=CH-P(O)(OEt)Ph | 76 |
| 30 | Ph-C≡CH | CH₂=C(Ph)-P(O)(OEt)Ph | 99 |
| 31 | NC-(CH₂)₃-C≡CH | NC-(CH₂)₃-C(=CH₂)-P(O)(OEt)Ph | 95 |
| 32 | HO-CH₂CH₂-C≡CH | HO-CH₂CH₂-C(=CH₂)-P(O)(OEt)Ph | 93 |
| 33 | Cl-(CH₂)₃-C≡CH | Cl-(CH₂)₃-C(=CH₂)-P(O)(OEt)Ph | 95 |
| 34 | cyclohexenyl-C≡CH | cyclohexenyl-C(=CH₂)-P(O)(OEt)Ph | 91 |

TABLE 2-continued

| Examples | Alkynes | Adducts | Yields (%) |
|---|---|---|---|
| 35 | 2-ethynylthiophene | 1-(thiophen-2-yl)vinyl-P(OEt)Ph(=O) | 77 |
| 36 | Me₃Si—≡ | Me₃Si-CH=CH-P(OEt)Ph(=O) | 63 |
| 37 | ≡—(CH₂)₅—≡ | (EtO)PhP(=O)-C(=CH₂)-(CH₂)₅-C(=CH₂)-P(OEt)Ph(=O) | 85 |
| 38 | Ph—≡—Ph | Ph-CH=C(Ph)-P(OEt)Ph(=O)  | 99 |

INDUSTRIAL APPLICABILITY

The present invention provides a process for the production of alkenylphosphine oxide compounds or alkenylphosphinic acid ester compounds which are useful as intermediates for the synthesis of physiologically active substances such as pharmaceuticals and agricultural chemicals, ligands for the preparation of catalysts, etc. in a high yield and a high utility. In accordance with the process for production according to the present invention, it is possible to easily, safely and efficiently synthesize the aimed alkenylphosphine oxide compounds or alkenylphosphinic acid esters by the reaction of acetylenes merely with phosphine oxide or hydrogen phosphinic acid ester and separation and purification of the product are easy as well. Accordingly, the present invention results in a great effect in industry.

The invention claimed is:

1. A process for the production of compound(s) represented by the formula [III]

$$R^1\{CH=CR^2[P(O)(R^3)(R_0^4)]\}_n \quad [III]$$

and/or the formula [IV]

$$R^1\{C[P(O)(R^3)(R_0^4)]=CHR^2\}_n \quad [IV]$$

($R^1$, $R^2$, $R^3$ and $R_0^4$ are the same as those defined below), characterized in that, a catalyst containing a metal of group 9 or group 10 of the periodic table is used and an acetylene compound represented by the formula [I]

$$R^1(C\equiv CR^2)_n \quad [I]$$

(in the formula, n is 1 or 2; $R^1$ and $R^2$ each when n is 1 and $R^2$ when n is 2 is hydrogen atom, an optionally substituted alkyl group, an optionally substituted cycloalkyl group, an optionally substituted alkenyl group, an optionally substituted cycloalkenyl group, an optionally substituted aryl group, an optionally substituted aralkyl group, an optionally substituted aryloxy group, an optionally substituted heteroaryl group, a ferrocenyl group, an optionally substituted alkoxy group or an optionally substituted silyl group; and $R^1$ when n is 2 is an optionally substituted alkylene group, an optionally substituted cycloalkylene group, an optionally substituted alkenylene group, an optionally substituted cycloalkenylene group, an optionally substituted arylene group, an optionally substituted aralkylene group, an optionally substituted arylenedioxy group, an optionally substituted heteroarylene group, a ferrocenylene group, an optionally substituted alkylenedioxy group or an optionally substituted silylenedioxy group) is made to react with a compound represented by the formula [II]

$$HP(O)(R^3)(R_0^4) \quad [II]$$

[in the formula, $R^3$ is an alkyl group, a cycloalkyl group, an aralkyl group or an aryl group and $R_0^4$ is $R^4$ or $OR^4$ (where $R^4$ is an alkyl group, a cycloalkyl group, an aralkyl group or an aryl group)].

2. The process for the production according to claim 1, wherein $R_0^4$ in the formula [II], the formula [III] and the formula [IV] is $R^4$.

3. The process for the production according to claim 2, wherein the metal of group 9 or group 10 of the periodic table is rhodium.

4. The process for the production according to claim 3, wherein the catalyst containing rhodium is a metallic rhodium species.

5. The process for the production according to claim 4, wherein the metallic rhodium species is rhodium black, rhodium powder or rhodium which is carried on a carrier.

6. The process for the production according to claim 3, wherein the catalyst containing rhodium is a rhodium complex catalyst.

7. The process for the production according to claim 6, wherein the rhodium complex catalyst is a complex catalyst containing no ligand.

8. The process for the production according to claim 6, wherein the rhodium complex catalyst is a rhodium complex catalyst in which tertiary phosphine or tertiary phosphite is a ligand.

9. The process for the production according to claim 6, wherein the rhodium complex catalyst is a precursor complex which is easily able to be converted to a low valence complex in a reaction system.

10. The process for the production according to claim 6, wherein the rhodium complex catalyst is a rhodium complex catalyst where tertiary phosphine and/or tertiary phosphite as ligand(s) which is formed in a reaction system using a rhodium complex containing neither tertiary phosphine nor tertiary phosphite as a ligand together with a tertiary phosphine and/or tertiary phosphite.

11. The process for the production according to claim 1, wherein $R_0^4$ in the formula [II], the formula [III] and the formula [IV] is $OR^4$.

12. The process for the production according to claim 11, wherein the metal of group 9 is rhodium.

13. The process for the production according to claim 11, wherein the metal of group 10 is palladium.

14. The process for the production according to claim 11, wherein the catalyst containing the metal of group 9 or group 10 of the periodic table is a low valence complex catalyst.

15. The process for the production according to claim 11, wherein the catalyst containing the metal of group 9 or group 10 of the periodic table is a low valence complex catalyst where tertiary phosphine or tertiary phosphite as a ligand.

16. The process for the production according to claim 11, wherein the catalyst containing the metal of group 9 or group 10 of the periodic table is a precursor complex which is able to be easily converted to a low valence in a reaction system.

17. The process for the production according to claim 11, wherein the catalyst containing the metal of group 9 or group 10 of the periodic table is a low valence complex where tertiary phosphine and/or tertiary phosphite as ligand(s) which is formed in are action system using the metal complex containing neither tertiary phosphine nor tertiary phosphite as a ligand together with a tertiary phosphine and/or tertiary phosphite.

18. The process for the production according to any of claims 11 to 17, wherein the reaction is carried out in the presence of a phosphinic acid represented by the formula [V]

$$HO-P(O)(R^5)_2 \qquad [V]$$

(in the formula, $R^5$ is an alkyl group, a cycloalkyl group or an aryl group).

* * * * *